United States Patent
Newmark et al.

(12) 
(10) Patent No.: US 6,264,995 B1
(45) Date of Patent: Jul. 24, 2001

(54) HERBAL COMPOSITION FOR REDUCING INFLAMMATION AND METHODS OF USING SAME

(76) Inventors: Thomas Newmark, 704 Cordell Ct., St. Louis, MO (US) 63132; Paul Schulick, 222 Kipling Rd., Brattleboro, VT (US) 05301

( * ) Notice: Subject to any disclaimer, the term of this patent is extended or adjusted under 35 U.S.C. 154(b) by 0 days.

(21) Appl. No.: 09/512,673

(22) Filed: Feb. 25, 2000

Related U.S. Application Data

(60) Provisional application No. 60/160,216, filed on Oct. 19, 1999.

(51) Int. Cl.[7] .......................... A01N 65/00; A61K 35/78; A61K 39/385
(52) U.S. Cl. ..................... 424/725; 424/729; 424/756
(58) Field of Search ................ 424/195.1, 725, 424/729, 756, 773, 779, 774

(56) References Cited

U.S. PATENT DOCUMENTS

| | | |
|---|---|---|
| 5,120,558 | 6/1992 | Nguyen et al. . |
| 5,494,668 | 2/1996 | Patwardhan . |
| 5,683,698 | 11/1997 | Chavali et al. . |
| 5,788,971 | 8/1998 | Togasaki . |
| 5,854,291 | 12/1998 | Laughlin et al. . |
| 5,874,084 * | 2/1999 | Yng-Wong ..................... 424/195.1 |
| 5,888,514 | 3/1999 | Weisman . |
| 5,891,440 * | 3/1999 | Lansky ............................ 424/195.1 |
| 5,908,628 * | 6/1999 | Hou ................................. 424/195.1 |
| 5,910,307 | 6/1999 | Kwak et al. . |
| 5,916,565 | 6/1999 | Rose et al. . |
| 5,932,101 | 8/1999 | Kanel et al. . |

* cited by examiner

*Primary Examiner*—Jon P. Weber
*Assistant Examiner*—Patrice A. Patten
(74) *Attorney, Agent, or Firm*—Patton Boggs LLP

(57) ABSTRACT

An herbal composition reducing inflammation in bones and joints by inhibiting the enzyme cyclooxygenase-2 is prepared from holy basil, turmeric, ginger, green tea, rosemary, huzhang, Chinese goldthread, barberry, oregano and *scutellariae baicalensis*. More particularly, the herbal composition of the present invention contains therapeutically effective amounts of the supercritical extracts of ginger, rosemary and oregano, and therapeutically effective amounts of extracts of holy basil, turmeric, green tea, huzhang, Chinese goldthread, barberry, rosemary and *scutellariae baicalensis*. The herbal composition can be administered orally, topically or parenterally. Particularly preferred embodiments are soft gel capsules for oral administration and creams for topical application. In addition to reducing inflammation, the herbal composition also promotes healthy joint function and, because it inhibits cyclooxygenase-2 (COX-2), the composition also promotes normal cell growth. Furthermore, the herbal composition contains organic anti-aging constituents that inactivate oxygen free radicals, thereby providing antioxidant benefits in addition to anti-inflammatory benefits.

10 Claims, No Drawings

HERBAL COMPOSITION FOR REDUCING INFLAMMATION AND METHODS OF USING SAME

This appln claims the benefit of Provisional No. 60/160,216 filed Oct. 19, 1999.

BACKGROUND OF THE INVENTION

This invention relates to herbal compositions. More particularly, this invention relates to an herbal composition capable of reducing inflammation in bones and joints. The present invention further relates to methods of using such herbal composition to reduce inflammation.

Arthritic disorders, including rheumatism, osteoarthritis, dysplasia, lupus, bursitis, and gout, are all characterized by inflammation and pain in bones, joints, muscles, and related connective tissues. Most of the forms are progressive. Bone and joint inflammation is a scourge of both animals and humans. Those who suffer from inflammation experience pain and discomfort and may, in advanced cases, lose the effective use of inflamed joints. Thus, the goal of therapeutic methods for treating bone or joint inflammation is the relief of pain and discomfort and the restoration of use of inflamed joints.

Certain enzymes appear to play a role in causing inflammation. One of the features of inflammation is increased oxygenation of arachidonic acid which is metabolized by two enzymic pathways—the cyclooxygenase (CO) and the 5-lipoxygenase (5-LO) pathways—leading to the production of prostaglandins and leukotrienes, respectively. Prostaglandins and leukotrienes are mediators of inflammation. Therapies designed to inhibit cydooxygenase and/or lipoxygenase activity are therefore of great interest.

There are two forms of the cyclooxygenase enzyme: cyclooxygenase-1 (COX-1) and cyclooxygenase-2 (COX-2). The latter form, i.e., COX-2, appears to play a key role in inflammatory processes. Recent scientific studies suggest that inhibiting the COX-2 enzyme may be an effective wayto reduce inflammation without the side effects associated with irreversible COX-1 inhibition. In addition, recent scientific studies also suggest that COX-2 inhibition may serve an important function in promoting normal cell growth in the colon, pancreas, breast tissue and other organ systems.

Drugs are being developed which are intended to selectively inhibit COX-2 with minimal effect on COX-1. However, despite the emphasis on COX-2 inhibition, these drugs appear to have serious side effects, e.g., a breakdown in digestive protective mucus and prevention of normal healing processes. For example, non-steroidal anti-inflammatory drugs (NSAIDS) can have a variety of toxic side effects such as, e.g., gastric erosion and adverse effects on kidneys and liver, and may inadequately regulate the cellular immune functions and secretions of various cytokines.

Natural ingredients, e.g., herbs, have also been used to treat bone and joint inflammation, especially in eastern countries, and, increasingly, in western countries. Compositions composed of natural ingredients and said to be useful in reducing inflammation are disclosed, e.g., in U.S. Pat. Nos. 5,494,668, 5,683,698, 5,916,565, 5,888,514, 5,908,628; 5,788,971; 5,854,291; and 5,910,307.

U.S. Pat. No. 5,494,668 (Patwardhan) discloses a method of treating degenerative musculoskeletal diseases such as rheumatoid arthritis and osteoarthritis in an animal, typically a human, involving administering to the animal, typically enterally, in a convenient dosage form, a therapeutically effective amount of the beneficiated extracts of the plants Ashwagandha, Sallai Guggul, Turmeric, and Ginger, in a predetermined proportion relative to each other with or without other biologically active inorganic ingredients.

U.S. Pat. No. 5,683,698 (Chavali et al.) discloses an herbal formulation and its use for reducing/alleviating symptoms associated with rheumatoid arthritis, osteoarthritis, and reactive arthritis and for reducing the production of pro-inflammatory cytokines. The formulation contains an herbal extract from the roots, rhizomes and/or vegetation of six herbal plant varieties, specifically, the species of Alpinia, Smilax, Tinospora, Tribulus, Withania, and Zingiber. The patent further discloses foods, beverages and medicaments in the form of capsules, tablets, liquids, and the like, containing the herbal formulation.

U.S. Pat. No. 5,916,565 (Rose et al.) discloses an orally administered composition for prophylaxis and therapy of joint and connective tissue disorders in vertebrates, wherein the composition contains metabolic precursors, herbal phytochemicals, and palatability agents. Suitable herbal phytochemicals are said to include cayenne, ginger, turmeric, yucca, Devil's claw, nettle leaf, Black Cohosh, alfalfa and celery seeds.

U.S. Pat. No. 5,888,514 (Weisman) discloses a composition for treating bone or joint inflammation in mammals, wherein the composition contains a systemically absorbable cartilage and an amninosaccharide and may optionally contain, among other ingredients, one or more extracts of an herb of the genus Withenia, of the bark of an herb of the genus Salix, or of a root of an herb of the genus Panax.

U.S. Pat. No. 5,908,628 (Hou) discloses compositions for treating osteoarthritis and rheumatoid arthritis, containing talc, silkworm excrement, and ingredients of plants of species of the genera Stephania, Coix, Pinellia, Prunus, Phellodendron, Sophora, Tetrapanax, Stemona, Glycyrrhiza, Tripterygium, Forsythia, and Siegesbeckia.

U.S. Pat. No. 5,788,971 (Togasaki) discloses an active oxygen free radical scavenging agent composed of green tea leaf extract containing epigallo catechin gallate and sunflower seed extract containing chlorogenic acid.

U.S. Pat. No. 5,854,291 (Laughlin, et al.) discloses a topically-applied pain reliever composition for treating such discomforts as arthritis pain, composed of capsaicin and, optionally, a plant extract selected from the group consisting of nettle extract, yarrow extract, coltsfoot extract, birch extract, rosemary extract, horsetail extract, ginger extract, chamomile extract, comfrey extract, lavender extract, and bergamot extract.

U.S. Pat. No. 5,910,307 (Kwak, et al.) discloses a combined medicinal plant composition for alleviating acute/chronic inflammation, composed of *Clematis Radix*, Trichosanthes root, and *Prunella Herba* (which contains oleanolic acid ursolic acid) in a certain ratio. The composition is also useful for inhibiting platelet/whole blood aggregation and inflammation-inducing enzymes (5-lipoxgenase, cylooxygenase-1 and cylooxygenase-2) and for scavenging toxic active oxygen species.

According to various studies, *ocimum sanctum* (holy basil) possesses significat anti-inflammatory properties and is capable of blocking both the cyclooxygenase and lipoxygenase pathways of arachidonate metablism. See e.g., *J. Ethnopharmacol.* April 1999; 65(1);13–9, *Evaluation of the Gastric Antiulcer Activity of Fixed Oil of Ocimun Sanctum (Holy Basil)*, Singh, S. Majundar DK College of Pharmacy, University of Delhi, India; *Indian J. Exp. Biol.* October 1998; 36(10): 1028–31, *Comparative Evaluation of Antiin-* flammatory Potential of Fixed Oil of Different Species of Ocimun and Its Possible Mechanism of Action, Singh S. College of Pharmacy (University of Delhi), Pushp Vihar, India; *J. Ethnopharmacol.* October 1996; 54(1):19–26, and *Evaluation of Anti-Inflammatory Potential of Fixed Oil of Ocimum Santum (Holy Basil) and Its Possible Mechanism of Action*, Singh, S., Majunbar D K, Rehan H M College of Pharmacy (University of Delhi), New Delhi, India. The marker constituents of *ocimum sanctum*, i.e., ursolic acid and oleanolic acid (less active) have been found to a significant COX-2 inhibitory effect. See, for example, *Indian J. Exp. Biol.* April 1997, 35(4):380–3, *Evaluation of Antiinflammatory Activity of Fatty Acids of Ocinum Sanctum Fixed Oil*, Singh S., Majumdar DK College of Pharmacy (University of Delhi) Pushp Vihar, New Delhi, India; and *FEBS Lett.* Mar. 16, 1992; 299(3):213–7, *Characterization of Uroslic Acid as a Lipoxygenase and Cyclooxygenase Inhibitor Using Macrophages, Platelets and Differentiated HL60 Leukemic Cells*, Najid A., Simon A., Cook J., Chable-Rabinovitch H., Delage C., Chulia A J, Rigaud M. *CJF INSERM* 88–03, Faculte de Medecine, Universite de Limoges, France; *J. Nat. Prod.* October 1998; 61(10); 1212–5, *Ursolic Acid from Plantago Major, a Selective Inhibitor of Cyclooxygenase-2 Catalyzed Protaglandin Biosynthesis*, Ringbom T., Segura L., Noreen Y., Perera P., Bohlin L. Divison of Pharmacognosy, Department of Pharmacy, Biomedical Centre, Uppsala University, Box 579, S-751 223 Uppsala, Sweden; *Cancer Res.* Feb. 15, 1998; 58(4):717–23 *Novel Triterpenoids Suppress Inducible Nitric Oxide Synthase (iNOS) and Inducible Cyclooxygenase (COX-2) in Mouse Macrophages*, Suh N., Honda T., Finlay H. J., Barchowsky A., Williams C., Benoit N. E., Xie Q. W., Nathan C., Gribble G. W., Sporn M. B., Department of Phamacology and Norris Cotton Cancer Center, Dartmouth Medical School, Hanover, N.H. 03755 USA; *Indian J. Exp. Biol.* December 1996; 34(12):1212–5, *Chemical and Pharmacological Studies on Fixed Oil of Ocimun Sanctum*; Singh S., Majumdar D. K., Yadov M. R., College of Pharmacy (University of Delhi) Pushp Vihar, India.; *J. Ethnopharmacol* November 1987, 21(2):153–63, *Ocinum Sanction: An Experimental Study Evaluating Its Anti-Inflammatory, and Analgesic and Antipyretic Activity in Animals*; Godhwani, S., Godhwani, J. L., Vyas D. S., Department of Phamacology and Experimental Therapeutics, Sandar Patel Medical College, Rajasthan, India.

Curcumin, a major principal of turmeric, has been found to directly inhibit the activity of COX-2. See, e.g., *Carcinogenesis* March 1999, 20(3):445–51, *Curcumin Inhibits Cyclooxgenase-2 Transcription in Bile Acid- and Phorbol Ester-Treated Human Gastrointestinal Epithelial Cells*, Zhang F., Altorki N. K., Mestre J. R., Subbaramiah K., Dannenberg A. J., Department of Cardiothoracic Surgery, New York Presbyterian Hospital and Weill Medical College of Cornell University, New York 10021, USA. See also, e.g., *Agents Actions* October 1982, 12(4):508–15, *Anti-Inflammatory and Irritant Activities of Curcumin Analogues in Rats*, Mukhopadhyay A., Basu N., Ghatak N., Gujral P. K; and *Int J Clin Pharmacol Ther Toxicol* December 1986, 24(12):651–4, *Evaluation of Anti-Inflammatory Property of Curcumin (Diferuloyl Methxane) in Patients with Postoperative Inflammation*, Satoskar R. R., Shah S. J., Shenoy S. G.

Melatonin, a constituent of ginger, has been found to exert potent anti-inflammatory effects via COX-2 inhibition. See, e.g., *J Pineal Res* August 1999, 27(1):9–14, *Regulation of Prostaglandin Production in Carrageenan-Induced Pleurisy by Melatonin*, Cuzzocrea S, Costantino G., Mazzon E., Caputi A. P., Institute of Pharmacology, School of Medicine, University of Messina, Italy; *Biochem Mol Biol Int* March 1995, 35(3):627–34, *Identifacation of Melatonin in Plants and Its Effects on Plasma Melatonin Levels and Binding to Melatonin Receptors in Vertebrates*, Hattori A., Migitaka H., Iigo M., Yamamoto K., Ohtani-Kaneko R., Hara M., Suzuki T., Reiter R. J., Department on Anatomy, St. Marianna University School of Medicine, Kawasaki, Japan. See also *Biomed Biochim Acta* 1984; 43(8–9):S335–46, *Aqueous Extracts of Onion, Garlic and Ginger Inhibit Platelet Aggregation and Alter Arachidonic Acid Metabolism*, Srivastava K. C.; and *Cancer Res* Mar. 1, 1996; 56(5):1023–30, *Inhibition of Tumor Promotion in SENCAR Mouse Skin by Ethanol Extract of Zingiber Officinale Rhizome*, Katiyar S. K., Agarwal R., Mukhtar H., Department of Dermatology, Skin Diseases Research Center, University Hospitals of Cleveland, Case Western Reserve University, Ohio.

Shogaol, a pungent component of ginger, has been found to inhibit cyclooxygenase. Reference is made, e.g., to *Nippon Yakurigaku Zasshi* October 1986; 88(4):263–9, *Pharmacological Studies on Ginger. IV. Effect of (6)-Shogaol on the Arachodonic Cascade*, Suekawa M., Yuasa K., Isono M., Sone H., Ikeya Y., Sakakibara I., Aburada M., Hosoya E.

Another constituent of ginger, eugenol, has also been found to be a 5-lipoxygenase inhibitor and to possess potent anti-inflammatory and/or anti-rheumatic properties. Reference is made, e.g., to *Pharmacology* November 1994, 49(5):314–8, *Suppressive Effects of Eugenol and Ginger Oil on Arthritic Rats*, Sharma J. N., Srivastava K. C., Gan E. K., Department Pharmacology, School of Medical Sciences, University of Science, Malaysia, Kelantan.

According to the USDA database, green tea contains six constituents having cyclooxygenase-inhibitor activity. According to the Napralert database, green tea contains fifty one constituents having anti-inflammatory activity. The polyphenos in green tea were found to cause a marked reduction in cyclooxygenase-2. Reference is made, e.g., to *Proc Natl Acad Sci USA* Apr. 13, 1999; 96(8):454–9, *Prevention of Collagen-Induced Arthritis in Mice by a Polyphenolic Fraction from Green Tea*, Haqqi T. M., Anthony D. D., Gupta S., Ahmad N., Lee M. S., Kumar G. K., Mukhtar H., Department of Medicine, Division of Rheumatic Diseases, Case Western Reserve University, 10900 Euclid Avenue, Cleveland, Ohio 44106. See also *Photochem Photobiol* November 1993, 58(5):695–700, *Protection Against Ultraviolet-B Radiation-Induced Local and Systemic Suppression of Contact Hypersensitivity and Edema Responses in C3H/HeN Mice by Green Tea Polyphenols*, Katiyar S. K., Elmets C. A., Agarwal R., Mukhtar H., Department of Dermatology, University Hospitals of Cleveland, Case Western Reserve University, Ohio 44106.

In addition, a group of compounds identified as flavan-3-ol derivatives (+)-catechin, rich in green tea, have been identified as COX-1 and COX-2 inhibitors, See, e.g., *Planta Med* August 1998; 64(6):520–4 *Flavan-3-ols isolated from some medicinal plants inhibiting COX-1 and COX-2 catalysed prostaglandin biosynthesis*. Noreen Y., Serrano G, Perera P., Bohlin L Department of Pharmacy, Uppsala University, Sweden; *J Nat Prod* January 1998; 61(1):8–12

*Two new isoflavones from Ceiba pentandra and their effect on cyclooxygenase-catalysed prostaglandin biosynthesis.* Noreen Y., el-Seedi H, Perera P., Bohlin L Department of Pharmacy, Uppsala University, Sweden; *J Nat Prod* January 1998; 61(1):2–7 *Development of a radiochemical cyclooxygenase-1 and -2 in vitro assay for identification of natural products as inhibitors of prostaglandin biosynthesis.* Noreen Y., Ringbom T., Perera P., Danielson H, Bohlin L Department of Pharmacy, Uppsala University, Sweden.

Salicylic acid, another constituent of green tea, also has been found to be a COX-2 inhibitor. Reference is made, e.g., to *Mol Pharmacol* June 1997, 51(6):907–12, *Sodium Salicylate Inhibits Cyclo-Oxygenase-2 Activity Independently of Transcription Factor (Nuclear Factor KappaB) Activation: Role of Adrachidonic Acid,* Mitchell J. A., Saunders M., Barnes P. J., Newton R., Belvisi M. G., Department of Anaesthesia and Critical Care Medicine, The Royal Brompton Hospital, London, England.

Berberine, found in barberry and Chinese goldthread, has been found to inhibit COX-2 without inhibiting COX-1 activity. Reference is made, e.g., to *J Ethnopharmacol* August 1999; 66(2):227–33 *Inhibition by berberine of cyclooxygenase-2 transcriptional activity in human colon cancer cells*; Fukuda K, Hibiya Y, Mutoh M, Koshiji M, Akao S, Fujiwana H Department of Oriental Medicine, Gifu University School of Medicine, Japan; and *Biol Pharm Bull* August 1998; 21(8):814–7 *Inhibitory effect of Coptidis Rhizoma and Scutellariae Radix on azoxymethane-induced aberrant crypt foci formation in rat colon.* Fukutake M, Yokota S, Kawamura H, Iisuka A, Amagaya S, Fukuda K, Komatsu Y Central Research Laboratories, Tsumura & Co., Ibaraki, Japan.

According to the USDA database, oregano is the source of the largest number of anti-inflammatory compounds.

*Scutellaria baicalensis* has been found to possess anti-inflammatory properties. See, e.g., *Planta Med* April 1995; 61(2):150–3 *Pharmacological effects of methanolic extract from the root of Scutellaria baicalensis and its flavonoids on human gingival fibroblast.* Chung C P, Park J B, Bae KH College of Dentistry, Seoul National University, Korea.

Other mediators of inflammation include oxygen-derived free radicals. Free radicals degrade hyaluronic acid, modify collagen and perhaps proteoglycan structure and/or synthesis, alter and interact with immunoglobulins, activate degradative enzymes and inactivate their inhibitors, and possibly participate in chemotaxis. It is desirable to provide a means for scavenging and detoxifying free radicals before they reach the affected area.

*Ocimum sanctum* (holy basil) has been found to possess antioxidant properties. Reference is made, for example to *Free Radic Res* August 1997; 27(2):221–8 *Evaluation of Antioxidant Effectiveness of a Few Herbal Plants,* Maulik G., Maulik N., Bhandari V., Kagan V. E., Pakrashi S., Das D. K., University of Connecticut School of Medicine, Farmington, Conn. 06030-1110, USA; and *Radiat Res* January 1999; 151(1):74–8, *In Vitro Radioprotection by Ocimum Flavenoids: Survival of Mice,* Uma Devi P., Ganasoundari A., Rao B. S., Srinivasan K. K., Department of Radiobiology, Kasturba Medical College, Manipal, India.

Rosemary is an antioxidant which may reduce COX-2 expression. Reference is made, e.g., *Cancer Res.* June 1, 1998; 58(11):2323–7 *Antioxidants reduce cylooxygenase-2 expression, prostaglandin production, and proliferation in colorectal cancer cells.* Chinery R, Beauchamp R D, Shyr Y, Kirkland S C, Coffey R J, Morrow JD Department of Medicine, The Vanderbilt Cancer Center, Vanderbilt University Medical Center, Nashville, Tenn. 37232, USA; *J Clin Invest* April 1995;95(4):1669–75 *Involvement of reactive oxygen intermediates in cyclooxygenase-2 expression induced by interleukin-1, tumor necrosis factor-alpha, and lipopolysaccharide.* Ferg L, Xia Y, Garcia G E, Hwang D, Wilson CB Department of Immunology, Scripps Research Instiute, La Jolla, Calif. 92037, USA.

Turmeric and curcumin have been found to offer as much antioxidant effect as vitamin E. Reference is made, for example to *Free Radic Biol Med* Jan. 1, 1998; 24(1):49–54, *Effect of Tumeric, Tumerin and Curcumin on H2O2-induced Renal Epithelial (LLC-PK1) Cell Injury*; Cohly H. H., Taylor A., Angel M. F., Salahudeen A. K., Department of Surgery (Plastic), University of Mississippi Medical Center, Jackson 39216, USA.

*Scutellaria baicalensis* has the ability to scavenge free radicals, Reference is made, e.g., to *Z Naturforsch* [C] November–December 1997;52(11–12):817–23 *Antioxidant activity of flavones from Scutellaria baicalensis in lecithin liposomes.* Gabrielska J, Oszmianski J, Zylka R, Komorowska M Department of Physics and Biophysics, Agricultural University, Norwida, Wroclaw; and *Res Commun Mol Pathol Pharmacol* October 1995;90(1):103–14 *Protection by baicalein against ascorbic acid-induced lipid peroxidation of rat liver microsomes.* Gao D, Sakurai K, Chen J, Ogiso T Shenyang College of Pharmacy, P.R. China.

Although herbal-containing compositions for reducing inflammation are know, it is continually desirable to provide alternative herbal compositions capable of reducing inflammation, particularly by inhibiting COX-2.

Accordingly, a primary object of this invention is to provide an herbal composition capable of effectively reducing bone and joint inflammation by inhibiting COX-2.

Another object of this invention is to provide an herbal composition capable of reducing inflammation while avoiding the side effects associated with traditional drug therapy.

A further object of this invention is to provide a COX-2-inhibiting herbal composition which not only has anti-inflammatory properties by also antioxidant properties.

A still further object of this invention is to provide an anti-inflammatory, COX-2-inhibiting herbal composition wherein the herbal extracts used are prepared without chemical solvents.

Yet another object of this invention is to provide an herbal composition having the characteristics set forth in the preceding objects, wherein the composition can be orally, topically or parenterally administered.

A further object of this invention is to provide methods of reducing inflammation using an herbal composition having the characteristics set forth in the preceding objects.

These objects and others are achieved in the present invention.

SUMMARY OF THE INVENTION

The present invention is based on the discovery that an herbal composition composed of specific herbs properly extracted and blended in correct proportions will safely and significantly inhibit COX-2, thereby reducing bone and joint inflammation and promoting normal cell growth.

Thus, one aspect of the present invention is directed to an herbal active-ingredient composition composed of therapeutically effective amounts of the supercritical extracts of ginger (preferably certified organic ginger), rosemary and oregano, and therapeutically effects of either regular or supercritical (preferably regular) extracts of holy basil, turmeric, green tea, huzhang, rosemary, Chinese goldthread, barberry, and scutellariae.

A further aspect of this invention is directed to a composition containing the herbal active-ingredient composition of this invention formulated together with a pharmaceutically acceptable carrier. In preferred embodiments, the active-ingredient composition is administered orally as a soft gel capsule or topically as a cream. A still further object of this invention is directed to methods of using the herbal composition to alleviate the symptoms associated with inflammation in persons afflicted with such symptoms.

By inhibiting COX-2, the herbal composition of this invention also promotes healthy joint function and normal cell growth.

In addition, the composition of this invention is capable of scavenging toxic active oxygen species, thereby providing antioxidant benefits.

Another benefit provided by the present invention is that the herbal composition can be prepared without using any chemical solvents. This is achieved by using a supercritical solvent-free extraction process to obtain the extracts. Such extraction process allows for the highest potency of active compounds in the extracts, as much as 250 times the potency of the original fresh plant material.

DETAILED DESCRIPTION OF THE INVENTION

As stated above, one aspect of the present invention provides an herbal active-ingredient composition which significantly inhibits the COX-2 enzyme, thereby reducing bone and joint inflammation.

The active-ingredient composition contains extracts from holy basil, turmeric, ginger, green tea, rosemary, huzhang, Chinese goldthread, barberry, oregano and *scuteilariae baicalensis*. As used herein, the term "extract" is intended to mean a concentrate of water-soluble and/or alcohol-soluble plant components from the portion of the plant extracted and can be in aqueous or powdered form.

In the present invention, the extracts from ginger, rosemary and oregano are obtained using a supercritical extraction process as discussed later herein. These extracts are referred to herein as "supercritical extracts". The extracts from holy basil, turmeric, green tea, huzhang, Chinese goldthread, barberry, rosemary and *scutellariae baicalensis* can be prepared using either a supercritical extraction process or a conventional extraction process. If prepared using a conventional extraction process, the extracts will be referred to herein as "regular extracts" as a means of distinguishing these extracts from the supercritical extracts. Preferably, the compositions and methods of this invention use regular extracts of the holy basil, turmeric, green tea, huzhang, Chinese goldthread, barberry, rosemary and *scutellariae baicalensis*.

Holy Basil (*ocimum sanctum*) contains the powerful COX-2 inhibitor, ursolic acid, which significantly enhances detoxification and reduces inflammation.

Turmeric contains a unique curcumin phytonutrient complex that naturally inhibits inflammatory COX-2. In addition, turmeric has been shown to possess antioxidant properties. Antioxidant activities diminish free radicals which aggravate the inflammatory response. Furthermore, recent studies have shown that tumeric is synergistic with green tea in that the presence of tumeric significantly multiplies the anti-inflammatory effect of green tea polyphenols.

Ginger inhibits both inflammatory COX-2 and 5-LOX and further functions as antioxidant. In the present invention, the ginger supercritical extract is preferably the supercritical extract of certified organic ginger.

Green tea contains polyphenols which markedly reduce COX-2. Green tea reportedly contains 51 anti-inflammatory phytonutrients.

The dual extracts of rosemary used in the present invention offer highly concentrated, full spectrum COX-2 inhibition and support detoxification.

Huzhang is the richest known source of resveratrol, which has been scientifically shown to inhibit inflammatory COX-2.

The Chinese goldthread and barberry supercritical extracts provide a unique berberine phytonutrient complex which naturally inhibits inflammatory COX-2.

Oregano is the source of the largest number (31) of anti-inflammatory compounds.

Scutellariae is a unique baicalin phytonutrient complex that naturally inhibits inflammatory COX-2.

As stated hereinabove, the herbal composition of this invention contains the supercritical extracts of ginger, rosemary and oregano. Supercritical extraction of these herbs can be carried out according to known supercritical extraction methods. Such methods are disclosed, e.g., in U.S. Pat. Nos. 5,932,101 and 5,120,558, which are hereby incorporated by reference herein.

U.S. Pat. No. 5,932,101 discloses a supercritical extraction process wherein an extraction solvent and a fluid feed are supplied with a countercurrent flow to an extraction column. The extraction solvent contains a dense gas (e.g., carbon dioxide), and the fluid feed contains at least one solute (e.g., an herb) and a carrier fluid (e.g., water). The solute is selective to the extraction solvent with respect to the carrier fluid. The carrier fluid contains at least one component which is barely soluble in the extraction solvent and substantially immiscible with the extraction solvent so as to provide two phases. The fluid feed and the extraction solvent intimately contact one another in the column for a sufficient amount of time to extract the solute from the carrier fluid to the extraction solvent. The column operates in an enhanced solubility region having a pressure of between 450 and 1200 bar and a temperature of between 50° C. and 300° C. The column has a diameter greater than about 3.5 centimeters and a height to diameter ratio of greater than about 5. A raffinate containing the carrier fluid is removed from the column, as is an extract containing the extraction solvent and the solute. The combination of pressure and temperature is sufficient for the solubility of the solute in the extraction solvent to be at least 250% by weight greater than the solubility of the solute in the extraction solvent at the same operating temperature but at 200 bar pressure. Additionally, the solute may be separated from the extraction solvent in a phase separation device such as a decanter, a coalescer, a cyclone and a second extraction column.

The supercritical extraction process disclosed in U.S. Pat. No. 5,120,558 involves grinding a spice or herb and then extracting the ground spice or herb with supercritical fluid carbon dioxide under a pressure of from about 400 bar to about 600 bar and at a temperature of from about 80° C. to about 120° C. At least one oleoresin fraction is precipitated from the loaded supercritical fluid under a pressure of from about 280 bar to about 380 bar and at a temperature of from about 80° C. to about 100° C. Additional oleoresins may be obtained by next adjusting the pressure of the supercritical fluid to from about 100 bar to about 200 bar within the same temperature range of 80° C. to 100° C., and finally by reducing the pressure to from about 30 bar to about 50 bar and the temperature to from about 0° C. to about 30° C.

The holy basil, turmeric, green tea, huzhang, Chinese goldthread, barberry, and *scutellariae baicalensis* extracts used in the present invention can be prepared using either conventional or supercritical extraction techniques. Suitable conventional extraction techniques are disclosed, e.g., in U.S. Pat. Nos. 5,891,440; 5,874,084; and 5,908,628; all of which are hereby incorporated by reference herein.

For example, the regular extracts used in the herbal composition of this invention can be prepared by contacting the herb with an appropriate solvent to form the extract. To make the extract suitable for oral administration, the solvent used must be substantially non-toxic to the subject so that there is no untoward level of adverse side effects, such as toxicity, irritation, allergy or hypersensitivity responses. The level of any such side effects should be commensurate with acceptable risk/benefit ratios. Examples of such substantially non-toxic solvents include water and ethanol.

In one extraction method which can be used herein, the plant portion to be extracted is placed into an extractor, 70% ethanol is added, and the resultant mixture is heated under reflux. Ethanol is recovered and condensed under low temperature and decompression until the specific density reaches 1.38 (thermal assay). The extract is then collected by vacuum drying.

The active-ingredient herbal composition of this invention can be prepared, for example, by individually washing, drying and grinding the herbs into fine powder, and then extracting the ground herbs (via supercritical extraction in the case of ginger, rosemary and oregano; and via either supercritical extraction or conventional extraction for the other herbs in the composition of this invention). The resulting extracts are then mixed together in amounts that are physiologically acceptable to the patient. No special mixing means is required. The mixture of extracts can be encapsulated, tableted or formulated with a physiologically acceptable vehicle into unit dosages.

The active-ingredient composition of this invention contains therapeutically effective amounts of the supercritical extracts of ginger, rosemary and oregano and therapeutically effective amounts of the regular extracts of holy basil, turmeric, green tea, rosemary, huzhang, Chinese goldthread, barberry, and *scutellariae baicalensis*. With respect to the herbal extracts used in the active-ingredient composition of the present invention, the term "therapeutically effective amount" means that amount of the extract which, in conjunction with the amounts of the other herbal extracts present in the composition, will promote the ability of the overall composition to reduce inflammation in bones and joints.

As stated previously herein, the herbal composition of this invention can be administered in a variety of ways, including orally, topically (including ophtamically, vaginally, rectally, intranasally, and the like), and parenterally (e.g., by intravenous drip or by intraperitoneal, subcutaneous or intramuscular injection). Most preferably, the composition of this invention is administered orally or topically.

The orally administered embodiments of the herbal composition of this invention can be in any conventional form such as, e.g., capsules (hard or soft), tablets, elixirs, powders, granules, suspensions in water or non-aqueous media, sachets, as additives to food or beverages, or even can be made into a tea. Most preferably, the orally administered embodiment of the composition is in the form of a soft gel capsule which is swallowed with water.

For preparing solid orally administered compositions such as capsules or tablets, the principal active ingredients are mixed with a pharmaceutical carrier (e.g., conventional tableting ingredients such as corn starch, lactose, sucrose, sorbitol, talc, stearic acid, magnesium stearate, dicalcium phosphate or gums) and other pharmaceutical diluents (e.g., water) to form a solid preformulation composition containing a substantially homogenous mixture of the composition of this invention, or a non-toxic pharmaceutically acceptable salt thereof. When referring to the preformulation compositions as substantially homogenous, it is meant that the active ingredients are dispersed evenly throughout the composition so that the composition may be readily subdivided into equally effective unit dosage forms such as capsules, pills and tablets. This solid preformulation composition can then be subdivided into unit dosage forms containing, for example, from 0.15 to 1.0 gram, of the active-ingredient composition.

Liquid preparations for oral administration may take the form of, for example, solutions, syrups or suspensions, or they may be presented as a dry product for reconstitution with water or other suitable vehicles before use. Such liquid preparations may be prepared by conventional means with pharmaceutically acceptable additives such as suspending agents (e.g., sorbitol syrup, methyl cellulose, or hydrogenated edible fats); emulsifying agents (e.g., lecithin or acacia); non-aqueous vehicles (e.g., almond oil, oily esters or ethyl alcohol); preservatives (e.g., methyl or propyl p-hydroxybenzoates or sorbic acid); and artificial or natural colors and/or sweeteners.

The herbal composition of this invention can be combined with a physiologically acceptable oral vehicle into unit dosages. A unit dosage can comprise a therapeutically effective amount of each herbal extract for a single daily administration (e.g., orally), or it can be formulated into smaller quantities of each ingredient to provide for multiple doses in a day. A unit dosage will depend upon many factors including age, size, and condition of the individual being treated and the number of times the unit will be taken in a single day. In any event, the entire daily dosage will be that which is physiologically acceptable to an individual and can be administered daily over a prolonged period of time. In the present invention, normally between about 300 and 2000 mg of the active herb composition is preferably orally administered per day, with part of the total dose preferably taken at two or more different times during the day. When the orally administered composition is in the form of a capsule, the serving size of the composition is typically two capsules, with each capsule preferably containing from 0.15 to 1.0 gram of the active composition.

Formulations for topical administration may include but are not limited to lotions, ointments, gels, creams, suppositories, drops, liquids, sprays, and powders. Conventional pharmaceutical carriers; aqueous, powder or oily bases; thickeners and the like may be necessary or desirable. Most preferably, the topically administered embodiment of the composition of this invention is in the form of a cream.

Formulations for parenteral administration may include but are not limited to sterile aqueous solutions which may also contain buffers, diluents and other suitable additives. The active ingredients may be formulated for parenteral administration by injection, which includes using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as stabilizing, suspending or dispersing agents. Alternatively, the active ingredients may be in powder form for reconstitution with a suitable vehicle, e.g., sterile pyrogert-free water, before use.

The exact proportion of the extracts used in the composition of this invention will depend on the concentration of active ingredients found naturally in each component. Using the guidance provided herein and a basic knowledge of drug preparation and pharmacology, one skilled in the art could easily adjust the proportions of the separate components of the composition so as to obtain a composition which has the therapeutic effects discussed herein.

The present invention is also directed to methods of reducing inflammation, involving orally, topically or parenterally administering an effective amount of the active-ingredient herbal composition of this invention to an individual in need of inflammation reduction. The term "effective amount" with respect to the active-ingredient herbal composition means that amount sufficient to alleviate the symptoms associated with inflammation. The effective amount will depend upon the severity of the symptoms and on the responsiveness of the patient to the herbal composition. Persons of ordinary skill in the art can easily determine optimum dosages, dosing methodologies, and repetition rates.

For topical use, the composition is preferably administered as a cream.

Suitable modes of parenteral administration include, e.g., intravenous drip; intraperitoneal, subcutaneous or intramuscular injection; and the like.

Oral administration is accomplished by ingesting the composition. As stated previously herein, the most preferred form of the orally administered composition of this invention is the soft gel capsule, which is preferably swallowed with water.

Presented in the table below is a particularly preferred embodiment of the orally administered soft gel capsule form of the composition of this invention. The formulation below is the combined compositions of two capsules. In other words, two capsules constitute a single serving or unit dose of the composition. Each capsule contains a portion of the overall active-ingredient composition.

TABLE

Orally Administered Herbal Composition:
Formulation Per Serving (Two Soft Gel Capsules)

| Ingredient | Amount (milligrams) |
| --- | --- |
| Holy Basil, leaf, extract (2% ursolic acid - 2 mg) | 100 |
| Turmeric, rhizome, extract (7% curcumin - 2.8 mg) | 100 |
| Ginger, rhizome, certified organic, supercritical extract (minimum 20% pungent compounds - 20 mg, 5% zingiberene - 5 mg) | 100 |
| Green Tea, leaf, extract (45% polyphenols - 45 mg) | 100 |
| Rosemary, leaf & essential oil, supercritical extract (23% total phenolic antioxidants [TPA] - 2.3 mg) | 100 |
| Huzhang, root, extract, radix & rhizome (8% resveratrol - 6.4 mg) | 80 |
| Rosemary, leaf, extract, 5:1 | 50 |
| Chinese Goldthread, root, extract (6% berberine - 2.4 mg) | 40 |
| Barberry, root, extract (6% berberine - 2.4 mg) | 40 |
| Oregano, leaf, supercritical extract (0.8% TPA - 0.32 mg) | 40 |
| *Scutellariae baicalensis*, root, extract, 5:1 | 20 |

The composition set forth in the table above preferably further contains olive oil (certified organic) and yellow beeswax.

The soft gel capsules containing the composition set forth in the table above are preferably composed of gelatin, vegetable glycerine, purified water and carob.

For oral administration of the above-recited formulation, two soft gel capsules (together constituting one serving are preferably taken daily, with 8 ounces of water.

What is claimed is:

1. An anti-inflammatory herbal composition, comprising about 13% by weight of a supercritical carbon dioxide of ginger, about 13% by weight of a supercritical carbon dioxide extract of rosemary; about 13% by weight of a supercritical carbon dioxide extract of oregano; about 13% by weight of an alcoholic, aqueous, hydroalcoholic or supercritical carbon dioxide extract of holy basil; about 13% by weight of an alcoholic, aqueous, hydroalcoholic or supercritical carbon dioxide extract of turmeric; about 13% by weight of an alcoholic, aqueous, hydroalcoholic or supercritical carbon dioxide extract of green tea; about 10.4% by weight of an alcoholic, aqueous, hydroalcoholic or supercritical carbon dioxide extract of huzhang; about 13% by weight of an alcoholic, aqueous, or hydroalcoholic extract of rosemary about 5.2% by weight of an alcoholic, aqueous, hydroalcoholic or supercritical carbon dioxide extract of Chinese goldthread; about 5.2% by weight of an alcoholic, aqueous, hydroalcoholic or supercritical carbon dioxide extract of barbeny; and about 2.6% by weight of an alcoholic, aqueous, hydroalcoholic or supercritical carbon dioxide extract of scutellariae.

2. A composition according to claim 1, wherein the composition is an orally administered composition.

3. A composition according to claim 2, wherein the orally administered composition is in a form selected from the group consisting of capsules, tablets, elixirs, powders, granules, suspensions, sachets, food additives, beverage additives, and tea.

4. A composition according to claim 2, wherein the orally administered composition is in the form of two soft gel capsules.

5. A composition according to claim 1, wherein the composition is a topically administered composition.

6. A composition according to claim 5, wherein the topically administered composition is in a form selected from the group consisting of lotions, ointments, gels, creams, suppositories, drops, liquids, sprays and powders.

7. A composition according to claim 6, wherein the topically administered composition is in the form of a cream.

8. A composition according to claim 1, wherein: the holy basil leaf alcoholic, aqueous, hydroalcoholic or supercritical carbon dioxide extract contains about 2% by weight of ursolic acid; the turmeric rhizome alcoholic, aqueous, hydroalcoholic or supercritical carbon dioxide extract contains about 7% by weight of curcumin; the ginger rhizome supercritical carbon dioxide extract contains about 5% by weight of zingiberene; the green tea leaf alcoholic, aqueous, hydroalcoholic or supercritical carbon dioxide extract contains about 45% by weight of polyphenols; the rosemary leaf and essential oil supercritical carbon dioxide extract contains about 23% by weight of phenolic antioxidants; the huzhang alcoholic, aqueous, hydroalcoholic or supercritical carbon dioxide extract contains about 8% by weight of resveratrol; the Chinese goldthread root alcoholic, aqueous, hydroalcoholic or supercritical carbon dioxide extract contains about 6% by weight of berberine; the barberry root alcoholic, aqueous, hydroalcoholic or supercritical carbon dioxide extract contains about 6% by weight of berberine; and the oregano leaf supercritical carbon dioxide extract contains about 0.8% by weight of phenolic antioxidants.

9. A composition according to claim 1, further comprising olive oil, yellow beeswax, gelatin, glycerine, purified water and carob.

10. A composition according to claim 1, wherein the composition is a parenterally administered composition.

* * * * *